US012232826B2

(12) United States Patent
Sowards et al.

(10) Patent No.: US 12,232,826 B2
(45) Date of Patent: Feb. 25, 2025

(54) MEDICAL DEVICE MAGNETIZER SYSTEM WITH INDICATORS

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 222 days.

(21) Appl. No.: 17/846,973

(22) Filed: Jun. 22, 2022

(65) Prior Publication Data

US 2022/0401158 A1 Dec. 22, 2022

Related U.S. Application Data

(60) Provisional application No. 63/213,539, filed on Jun. 22, 2021.

(51) Int. Cl.
*A61B 34/20* (2016.01)
*A61B 17/00* (2006.01)
(Continued)

(52) U.S. Cl.
CPC .............. *A61B 34/20* (2016.02); *A61B 90/98* (2016.02); *H01F 13/00* (2013.01);
(Continued)

(58) Field of Classification Search
CPC ..... A61B 34/20; A61B 90/98; A61B 17/3403; A61B 2017/00876; A61B 2034/2051;
(Continued)

(56) References Cited

U.S. PATENT DOCUMENTS 3,409,853 A 11/1968 Guerth
3,467,926 A 9/1969 Smith
(Continued)

FOREIGN PATENT DOCUMENTS

CN 105025787 A 11/2015
CN 105232047 A 1/2016
(Continued)

OTHER PUBLICATIONS

EP 18790656.5 filed Nov. 27, 2019 Supplementary European Search Report dated Apr. 9, 2020.
(Continued)

*Primary Examiner* — Thienvu V Tran
*Assistant Examiner* — Sreeya Sreevatsa
(74) *Attorney, Agent, or Firm* — Rutan & Tucker LLP (57) ABSTRACT

A magnetizer system for use with a medical device including ferrous elements. The magnetizer can include a magnetizer body defining a cavity, the magnetizer body having a body opening in communication with the cavity, the magnetizer body including one or more magnets configured to generate a magnetic field configured to imprint a magnetic signature on ferrous elements within the cavity. The magnetizer can include one or more mechanisms configured to detect the presence of the medical device.

26 Claims, 7 Drawing Sheets

(51) Int. Cl.
*A61B 17/34* (2006.01)
*A61B 90/98* (2016.01)
*A61M 25/01* (2006.01)
*H01F 13/00* (2006.01)

(52) U.S. Cl.
CPC . *A61B 2017/00876* (2013.01); *A61B 17/3403* (2013.01); *A61B 2034/2051* (2016.02); *A61M 25/0127* (2013.01)

(58) Field of Classification Search
CPC ...... A61B 5/06; H01F 13/00; A61M 25/0127; G06K 7/10297; G06K 17/0029; G16H 40/60
USPC ........................................................ 361/143
See application file for complete search history.

(56) References Cited

U.S. PATENT DOCUMENTS

| | | |
|---|---|---|
| 3,847,157 A | 11/1974 | Caillouette et al. |
| 4,063,561 A | 12/1977 | McKenna |
| 4,161,943 A | 7/1979 | Nogier |
| 4,237,518 A | 12/1980 | Krulwich |
| 4,458,705 A | 7/1984 | Cawood |
| 4,529,954 A | 7/1985 | Steingroever et al. |
| 4,633,237 A * | 12/1986 | Tucknott ............. A61B 5/1117 600/595 |
| 5,055,813 A | 10/1991 | Johnson |
| 5,659,279 A | 8/1997 | Janssen et al. |
| 5,803,089 A | 9/1998 | Ferre et al. |
| 5,845,646 A | 12/1998 | Lemelson |
| 6,154,352 A | 11/2000 | Atallah |
| 6,249,199 B1 | 6/2001 | Liu |
| 6,310,532 B1 | 10/2001 | Santa Cruz et al. |
| 6,432,036 B1 | 8/2002 | Kim |
| 7,023,309 B2 | 4/2006 | Laskaris et al. |
| 7,090,639 B2 | 8/2006 | Govari |
| 7,135,978 B2 | 11/2006 | Gisselberg et al. |
| 7,214,191 B2 | 5/2007 | Stringer et al. |
| 7,775,215 B2 | 8/2010 | Hassler, Jr. et al. |
| 7,775,966 B2 | 8/2010 | Dlugos et al. |
| 7,850,006 B2 | 12/2010 | Uchiyama |
| 7,873,401 B2 | 1/2011 | Shachar |
| 7,887,516 B2 | 2/2011 | Young |
| 7,927,270 B2 | 4/2011 | Dlugos et al. |
| 8,016,744 B2 | 9/2011 | Dlugos et al. |
| 8,016,745 B2 | 9/2011 | Hassler, Jr. et al. |
| 8,174,346 B1 | 5/2012 | Koren |
| 8,240,211 B2 | 8/2012 | Zeitner et al. |
| 8,388,541 B2 | 3/2013 | Messerly et al. |
| 8,475,407 B2 | 7/2013 | Kalpin et al. |
| 8,483,802 B2 | 7/2013 | Kalpin et al. |
| 8,532,743 B2 | 9/2013 | Stangenes et al. |
| 8,622,975 B2 | 1/2014 | Andreoni et al. |
| 8,725,435 B2 | 5/2014 | Snow et al. |
| 8,781,555 B2 | 7/2014 | Burnside et al. |
| 8,840,541 B2 | 9/2014 | Snow et al. |
| 8,849,382 B2 | 9/2014 | Cox et al. |
| 8,939,888 B2 | 1/2015 | Augarten et al. |
| 9,017,283 B2 | 4/2015 | Birchard et al. |
| 9,113,812 B2 | 8/2015 | Kalpin et al. |
| 9,155,517 B2 | 10/2015 | Dunbar et al. |
| 9,216,257 B2 | 12/2015 | Kalpin et al. |
| 9,224,529 B2 | 12/2015 | Gery |
| 9,257,220 B2 | 2/2016 | Nicholls et al. |
| 9,299,925 B2 | 3/2016 | Yi et al. |
| 9,308,022 B2 | 4/2016 | Chitre et al. |
| 9,339,601 B2 | 5/2016 | Kalpin et al. |
| 9,439,653 B2 | 9/2016 | Avneri et al. |
| 9,456,766 B2 | 10/2016 | Cox et al. |
| 9,459,087 B2 | 10/2016 | Dunbar et al. |
| 9,492,097 B2 | 11/2016 | Wilkes et al. |
| 9,517,299 B2 | 12/2016 | Tieck et al. |
| 9,521,961 B2 | 12/2016 | Silverstein et al. |
| 9,554,716 B2 | 1/2017 | Burnside et al. |
| 9,597,008 B2 | 3/2017 | Henkel et al. |
| 9,636,031 B2 | 5/2017 | Cox |
| 9,649,048 B2 | 5/2017 | Cox et al. |
| 9,744,291 B2 | 8/2017 | Tieck et al. |
| 10,032,552 B2 | 7/2018 | Ma et al. |
| 10,449,330 B2 | 10/2019 | Newman et al. |
| 10,524,691 B2 | 1/2020 | Newman et al. |
| 10,751,509 B2 | 8/2020 | Misener |
| 11,344,220 B2 | 5/2022 | Burkholz et al. |
| 11,369,410 B2 | 6/2022 | Lindekugel |
| 2003/0040671 A1 | 2/2003 | Somogyi et al. |
| 2003/0052785 A1 | 3/2003 | Gisselberg et al. |
| 2004/0019447 A1 | 1/2004 | Shachar |
| 2004/0051610 A1 | 3/2004 | Sajan |
| 2005/0059884 A1 | 3/2005 | Krag |
| 2006/0114088 A1 | 6/2006 | Shachar |
| 2006/0211914 A1 | 9/2006 | Hassler et al. |
| 2007/0244373 A1 | 10/2007 | Osypka |
| 2007/0290654 A1 | 12/2007 | Govari et al. |
| 2008/0049367 A1 | 2/2008 | Carson et al. |
| 2008/0146939 A1 | 6/2008 | McMorrow et al. |
| 2010/0043561 A1 | 2/2010 | Zeitner et al. |
| 2010/0096553 A1* | 4/2010 | Patil ..................... G01S 17/04 250/341.8 |
| 2010/0210950 A1 | 8/2010 | Dunbar et al. |
| 2011/0060185 A1 | 3/2011 | Ikuma et al. |
| 2011/0196235 A1 | 8/2011 | Dunbar et al. |
| 2011/0237936 A1 | 9/2011 | Kalpin et al. |
| 2011/0237937 A1 | 9/2011 | Kalpin et al. |
| 2013/0150714 A1 | 6/2013 | Howlett et al. |
| 2013/0296691 A1 | 11/2013 | Ashe |
| 2014/0031674 A1 | 1/2014 | Newman et al. |
| 2014/0165796 A1 | 6/2014 | Gauthier et al. |
| 2014/0253270 A1* | 9/2014 | Nicholls ................ A61B 5/062 335/284 |
| 2014/0257080 A1 | 9/2014 | Dunbar et al. |
| 2014/0257104 A1 | 9/2014 | Dunbar et al. |
| 2014/0257746 A1 | 9/2014 | Dunbar et al. |
| 2015/0080710 A1 | 3/2015 | Henkel et al. |
| 2015/0359991 A1 | 12/2015 | Dunbar et al. |
| 2015/0365787 A1 | 12/2015 | Farrell |
| 2016/0015472 A1* | 1/2016 | Tiernan .................. D04H 1/413 600/424 |
| 2016/0351312 A1 | 12/2016 | Koren |
| 2017/0007200 A1 | 1/2017 | Hagy et al. |
| 2017/0079548 A1 | 3/2017 | Silverstein et al. |
| 2017/0079549 A1 | 3/2017 | Henkel et al. |
| 2017/0079550 A1 | 3/2017 | Henkel et al. |
| 2017/0079551 A1 | 3/2017 | Henkel et al. |
| 2017/0126864 A1 | 5/2017 | Lim et al. |
| 2017/0261564 A1 | 9/2017 | Gabrys et al. |
| 2017/0325713 A1* | 11/2017 | Burkholz ................ A61M 5/32 |
| 2017/0326342 A1 | 11/2017 | Ma et al. |
| 2018/0061546 A1 | 3/2018 | Ma et al. |
| 2018/0289929 A1* | 10/2018 | Ma .................... A61M 25/0127 |
| 2018/0310955 A1* | 11/2018 | Lindekugel ............ A61B 90/11 |
| 2019/0298221 A1 | 10/2019 | Sonderegger |
| 2020/0360662 A1 | 11/2020 | Ma et al. |
| 2021/0065857 A1 | 3/2021 | Newman et al. |
| 2021/0169585 A1 | 6/2021 | Prince et al. |
| 2022/0105324 A1 | 4/2022 | Broniec et al. |
| 2022/0142501 A1 | 5/2022 | Prince et al. |
| 2022/0142502 A1 | 5/2022 | Prince et al. |
| 2022/0323101 A1 | 10/2022 | Lindekugel et al. |
| 2023/0006443 A1 | 1/2023 | Patankar et al. |
| 2024/0090793 A1 | 3/2024 | Prince et al. |

FOREIGN PATENT DOCUMENTS

| | | |
|---|---|---|
| CN | 103945772 B | 9/2016 |
| CN | 105073067 B | 6/2017 |
| DE | 102006033229 B4 | 5/2013 |
| EP | 2015105 B1 | 6/2011 |
| EP | 2730306 A1 | 5/2014 |
| EP | 2285287 B1 | 4/2015 |
| EP | 2939599 A2 | 11/2015 |
| EP | 2939601 A2 | 11/2015 |
| EP | 2997901 A1 | 3/2016 |

(56) References Cited

FOREIGN PATENT DOCUMENTS

| | | | |
|---|---|---|---|
| EP | 2753243 | B1 | 4/2016 |
| JP | 5349582 | B2 | 11/2013 |
| JP | 5908981 | B2 | 4/2016 |
| JP | 6242421 | B2 | 12/2017 |
| KR | 20150123233 | A | 11/2015 |
| WO | 2008009442 | A2 | 1/2008 |
| WO | 2009010386 | A1 | 1/2009 |
| WO | 2009129845 | A1 | 10/2009 |
| WO | 2013034175 | A1 | 3/2013 |
| WO | 2013142386 | A1 | 9/2013 |
| WO | 2014/062728 | A1 | 4/2014 |
| WO | 2014135592 | A1 | 9/2014 |
| WO | 16096190 | A1 | 6/2016 |
| WO | 17016961 | A1 | 2/2017 |
| WO | 2018/201053 | A1 | 11/2018 |
| WO | 2022/099147 | A1 | 5/2022 |
| WO | 2022103772 | A1 | 5/2022 |
| WO | 2022271864 | A1 | 12/2022 |
| WO | 2023009446 | A1 | 2/2023 |

OTHER PUBLICATIONS

EP 221711096 filed May 2, 2022, Extended European Search Report dated Jul. 22, 2022.
EP20202521.9 filed Oct. 19, 2020 Extended European Search Report dated Jan. 28, 2021.
PCT/US2018/029958 filed Apr. 27, 2018 Communication Pursuant to Rules 70(2) and 70a(2) dated Apr. 29, 2020.
PCT/US2018/029958 filed Apr. 27, 2018 International Search Report and Written Opinion dated Jul. 11, 2018.
PCT/US2018/029958 filed Apr. 27, 2018 International Search Report dated Apr. 27, 2018.
PCT/US2021/058478 filed Nov. 8, 2021 International Search Report and Written Opinion dated Mar. 1, 2022.
U.S. Appl. No. 15/965,419, filed Apr. 27, 2018 Final Office Action dated Jan. 15, 2021.
U.S. Appl. No. 15/965,419, filed Apr. 27, 2018 Non-Final Office Action dated Aug. 6, 2021.
U.S. Appl. No. 15/965,419, filed Apr. 27, 2018 Non-Final Office Action dated Sep. 24, 2020.
U.S. Appl. No. 15/965,419, filed Apr. 27, 2018 Notice of Allowance dated Feb. 16, 2022.
PCT/US2021/058667 filed Nov. 9, 2021 International Search Report and Written Opinion dated Mar. 1, 2022.
PCT/US2022/034584 filed Jun. 22, 2022, International Preliminary Report on Patentability dated Dec. 14, 2023.
U.S. Appl. No. 17/521,680, filed Nov. 8, 2021 Non-Final Office Action dated Jun. 2, 2023.
U.S. Appl. No. 17/521,680, filed Nov. 8, 2021 Notice of Allowance dated Oct. 11, 2023.
U.S. Appl. No. 17/522,828, filed Nov. 9, 2021 Non-Final Office Action dated Nov. 9, 2023.
U.S. Appl. No. 17/850,468, filed Jun. 27, 2022 Restriction Requirement dated Dec. 29, 2023.
PCT/US2022/034584 filed Jun. 22, 2022, International Search Report and Written Opinion dated Oct. 10, 2022.
PCT/US2022/038202 filed Jul. 25, 2022 International Search Report and Written Opinion dated Nov. 14, 2022.
U.S. Appl. No. 17/522,828, filed Nov. 9, 2021 Notice of Allowance dated Apr. 3, 2024.
U.S. Appl. No. 17/850,468, filed Jun. 27, 2022 Notice of Allowance dated Sep. 5, 2024.
U.S. Appl. No. 17/872,814, filed Jul. 25, 2022 Non-Final Office Action dated Jul. 10, 2024.
U.S. Appl. No. 18/524,659, filed Nov. 30, 2023 Non-Final Office Action dated Jul. 29, 2024.

* cited by examiner

MEDICAL DEVICE MAGNETIZER SYSTEM WITH INDICATORS

PRIORITY

This application claims the benefit of priority to U.S. Provisional Application No. 63/213,539, filed Jun. 22, 2021, which is incorporated by reference in its entirety into this application.

BACKGROUND

A ferrous medical device can be magnetized for the purpose of tracking the medical device in three-dimensional space. The ferrous medical device can be brought into a magnetic field within a magnetizer, imprinting a magnetic signature onto the medical device that is able to be tracked in three-dimensional space. However, it can be difficult to determine if the medical device has been magnetized. It would be beneficial to a user to be able to determine if a medical device has been magnetized. Disclosed herein are a system and method of use that address the foregoing.

SUMMARY

Disclosed herein is a magnetizer system for use with a medical device including ferrous elements, the system including a magnetizer having a magnetizer body defining a cavity, the magnetizer body having a body opening in communication with the cavity, the magnetizer body including one or more magnets configured to generate a magnetic field configured to imprint a magnetic signature on ferrous elements within the cavity and one or more mechanisms configured to detect the presence of the medical device.

In some embodiments, the one or more mechanisms include an infrared detection system having one or more infrared emitters configured to generate an infrared beam across the cavity and one or more infrared sensors configured to detect the infrared beam, the infrared emitters and infrared sensors in communication with a console.

In some embodiments, the one or more mechanisms include a mechanical switch configured to transition between a non-magnetized configuration and a magnetized configuration.

In some embodiments, the magnetizer includes a RFID reader coupled to the magnetizer body or contained within the cavity, the RFID reader in communication with the console.

In some embodiments, the medical device includes a RFID tag configured to be detected by the RFID reader.

In some embodiments, the magnetic signature includes a monopole magnetic signature.

In some embodiments, the mechanical switch includes a hinge coupled to each of the mechanical switch and a lever arm, the lever arm protruding into the cavity and configured to be contacted by the medical device to transition the mechanical switch from the non-magnetized configuration to the magnetized configuration.

In some embodiments, the mechanical switch resides within a recess within the magnetizer body.

In some embodiments, the non-magnetized configuration includes the mechanical switch is perpendicular to the lever arm and residing fully within the recess.

In some embodiments, the magnetized configuration includes the mechanical switch moved away from the recess and the magnetizer body.

In some embodiments, the medical device including ferrous elements is selected from the group consisting of a needle, a catheter, and a combination.

In some embodiments, the magnetizer includes one or more sensors in communication with the console, the one or more sensors configured to detect and track the medical device using inductive sensing or optical sensing.

In some embodiments, the console includes one or more processors, an energy source, non-transitory computer-readable medium, and a plurality of logic modules.

In some embodiments, the one or more magnets include one or more electromagnets in communication with the energy source.

In some embodiments, the console is in wireless communication with one or more computing devices or an electronic medical record system.

In some embodiments, the plurality of logic modules, when executed by the processor, are configured to perform operations including activating the one or more infrared sensors and the one or more infrared emitters, detecting the RFID tag of the medical device, detecting the one or more infrared beams from the one or more infrared emitters, activating the one or more sensors, and detecting the medical device using the one or more sensors by inductive sensing or optical sensing.

Also disclosed herein is a method of imprinting a magnetic signature onto a medical device having ferrous elements using a magnetizer system including detecting the medical device with a magnetizer system having one or more mechanisms configured to detect the presence of the medical device, placing the medical device within a cavity of the magnetizer, confirming the medical device is within the cavity, and imprinting the magnetic signature onto the medical device.

In some embodiments, the magnetizer system includes a magnetizer having a magnetizer body defining the cavity, the magnetizer body having a body opening in communication with the cavity and one or more magnets configured to imprint the magnetic signature onto the medical device within the cavity; the magnetizer having one or more sensors in communication with a console, the one or more sensors configure to detect and track the medical device using inductive sensing or optical sensing; and the one or more mechanisms configured to detect the presence of the medical device include an infrared detection system in communication with the console; and a mechanical switch configured to transition between a non-magnetized configuration and a magnetized configuration.

In some embodiments, the magnetizer includes a RFID reader coupled to the magnetizer body or contained within the cavity, the RFID reader in communication with the console and configured to detect a RFID tag coupled to the medical device.

In some embodiments, detecting the medical device includes using the RFID reader to detect the RFID tag of the medical device.

In some embodiments, placing the medical device within the cavity of the magnetizer include slidably inserting the medical device within the cavity.

In some embodiments, confirming the medical device is within the cavity includes using the infrared detection system having one or more infrared emitters configured to generate an infrared beam across the cavity and one or more infrared sensors configured to detect the infrared beam.

In some embodiments, the infrared detection system confirms the medical device is within the cavity when the medical device breaks the infrared beam across the cavity.

In some embodiments, confirming the medical device is within the cavity includes confirming by a mechanical switch coupled to the magnetizer transitioned from a non-magnetized configuration to a magnetized configuration.

In some embodiments, the mechanical switch resides within a recess of the magnetizer body, having a hinge coupled to the mechanical switch and a lever arm, the lever arm protruding into the cavity and configured to be contacted by the medical device.

In some embodiments, imprinting the magnetic signature onto the medical device includes imprinting the magnetic signature onto the medical device as the medical device is removed from the cavity.

In some embodiments, the magnetic signature includes a monopole magnetic signature.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical, or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

Figure 1:
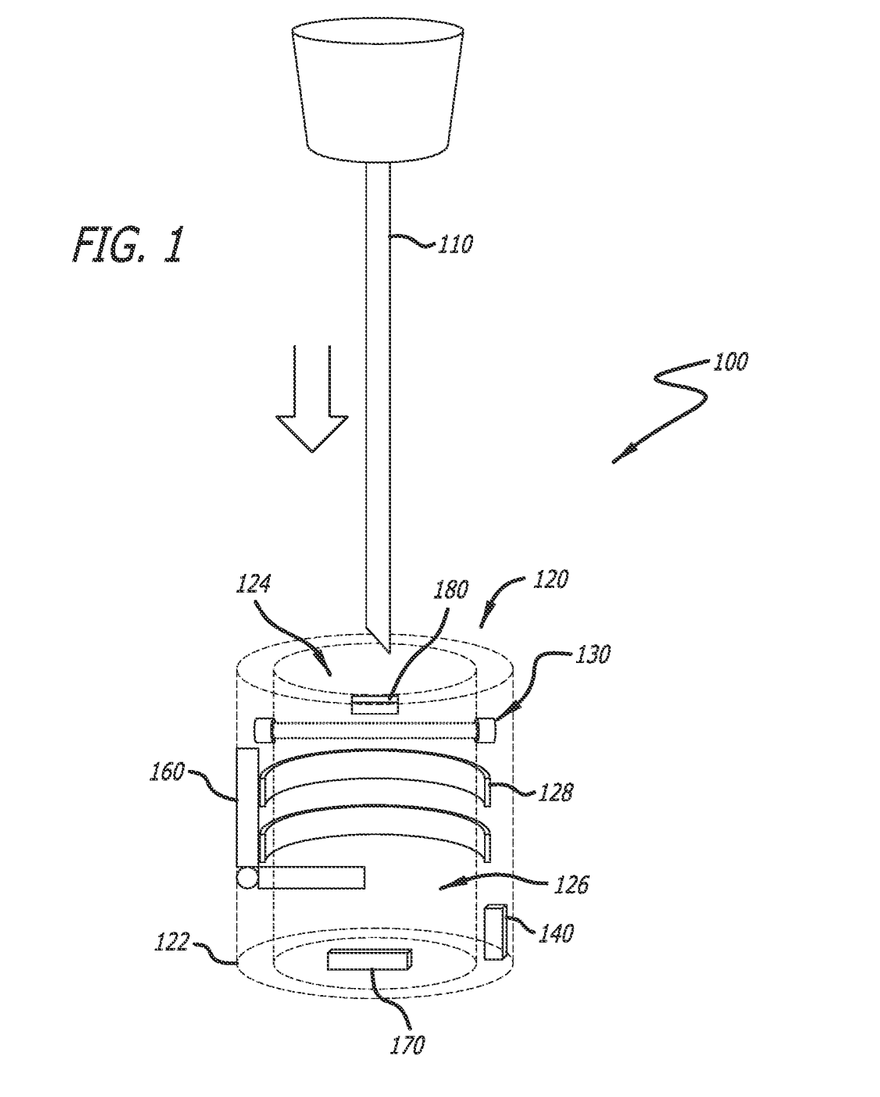
FIG. 1 illustrates a cross sectional view of a magnetizer system including a magnetizer and a medical device, in accordance with some embodiments.

FIG. 1 illustrates a cross sectional view of a magnetizer system 100 including a magnetizer 120 and a medical device 110, in accordance with some embodiments. In some embodiments, the magnetizer system 100 includes the magnetizer 120 configured to imprint a magnetic signature upon the medical device 110 having ferrous elements therein. The magnetic signature may allow tracking of the location and orientation of the medical device 110 in subsequent use. In some embodiments, the medical device 110 may include a needle, a vascular access device including a catheter, a peripherally inserted central catheter, or the like. In some embodiments, the magnetizer 120 includes a magnetizer body 122 defining a cavity 126 therein. The magnetizer 120 includes a body opening 124 in communication with the cavity 126, the body opening 124 allowing the medical device 110 to be slidably received therethrough. In some embodiments, the magnetizer body 122 may be shaped in a cylindrical prism, a rectangular prism or the like. The magnetizer 120 may be enabled with one or more mechanisms for detecting the presence of the medical device 110 within the cavity 126. Such detecting mechanisms may also indicate to a user that the medical device 110 has been inserted, or magnetized, or that the magnetizer 120 has been activated. In some embodiments, the detecting mechanisms may include one or more of an infrared detection system 130, a mechanical switch 160, one or more magnets 128 and/or a RFID reader 170. In some embodiments, the magnetizer 120 may include one or more sensors 180 configured to detect and track the medical device 110. The one or more sensors 180 may be coupled to the magnetizer 120 and/or may be located within the cavity 126. In some embodiments, the one or more sensors 180 may be wired to a console 140 or may be in wireless communication with the console 140. In some embodiments, the one or more sensors 180 may include sensors configured for inductive sensing or optical sensing of the medical device 110.

The magnetic signature may be consistent with differentiating information/data regarding the medical device 110 such that a first subset of a plurality of the medical devices 110 includes a magnetic signature that is different from the magnetic signature of a second subset of the plurality of the medical devices 110. In some embodiments, the differentiating information may include model information for the medical device 110, such as a module name or model number, for example. In some embodiments, the differentiating information may include dimensional information of the medical device 110, such as a length or diameter, for example. In some embodiments, the differentiating information may include manufacturing information for the medical device 110, such as a manufacturing date or lot number, for example. In some embodiments, the differentiating information may include unique information pertaining to the medical device 110, such as a serial number, for example. As such, in some embodiments, the magnetic signature for any one medical device 110 may be unique with respect to (i.e., different from) the magnetic signature for every other medical device 110.

Figure 2A:
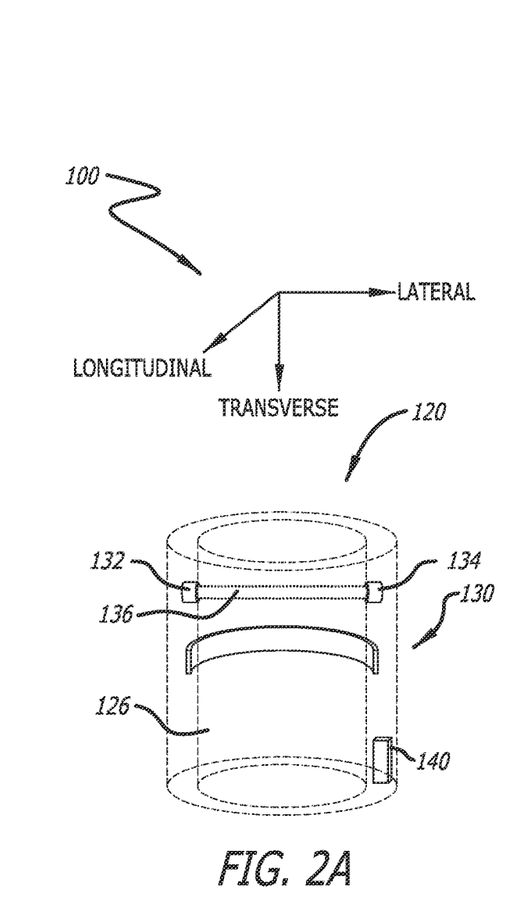
FIG. 2A illustrates a cross sectional view of the magnetizer having an infrared detection system, in accordance with some embodiments.

FIG. 2A illustrates a cross sectional view of the magnetizer 120 having the infrared detection system 130, in accordance with some embodiments. The infrared detection system 130 may include one or more infrared ("IR") emitters 132 and one or more corresponding IR sensors 134 in communication with the console 140. The one or more IR emitters 132 and one or more IR sensors 134 may be wired to the console 140 or in wireless communication with the console 140. In some embodiments, the IR emitters 132 and the IR sensors 134 may also include near infrared ("NIR") emitters and sensors. Each IR emitter 132 may be configured to emit an IR beam 136 spanning the cavity 126 so that the IR beam 136 is detected by the corresponding IR sensor 134. Each IR emitter 132 may be arranged laterally in line with each corresponding IR sensor 134. In some embodiments, the IR emitters 132 and corresponding IR sensors 134 may be located adjacent the body opening 124. In some embodiments, the IR emitter 132 may be configured to continuously emit the IR beam 136 and the IR sensor 134 may be configured to continuously detect the IR beam 136. In some embodiments, the IR emitter 132 may be configured to emit the IR beam 136 in accordance with a user defined interval cycle (e.g., every 5 milliseconds, every second or the like) and the IR sensor 134 may be configured to detect the IR beam 136 in accordance with the user defined interval cycle.

Figure 2B:
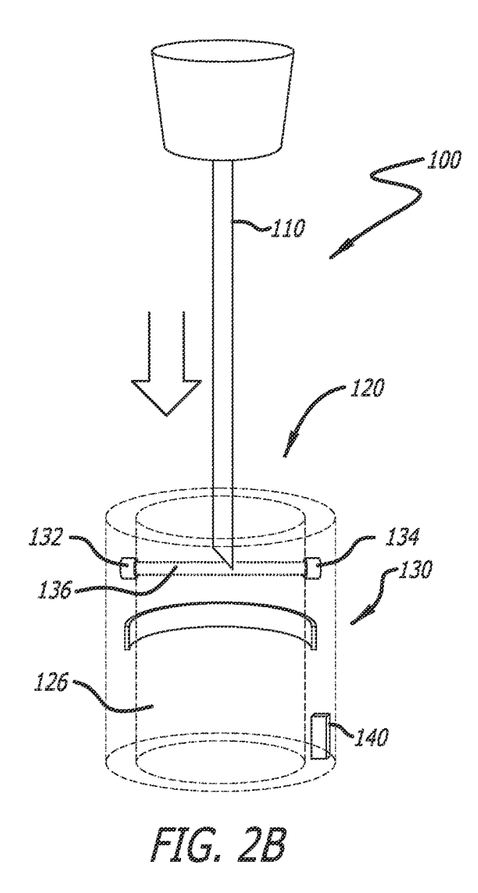
FIGS. 2B-2C illustrates a cross sectional view of the exemplary method of the infrared detection system detecting the medical device, in accordance with some embodiments.
Figure 2C:
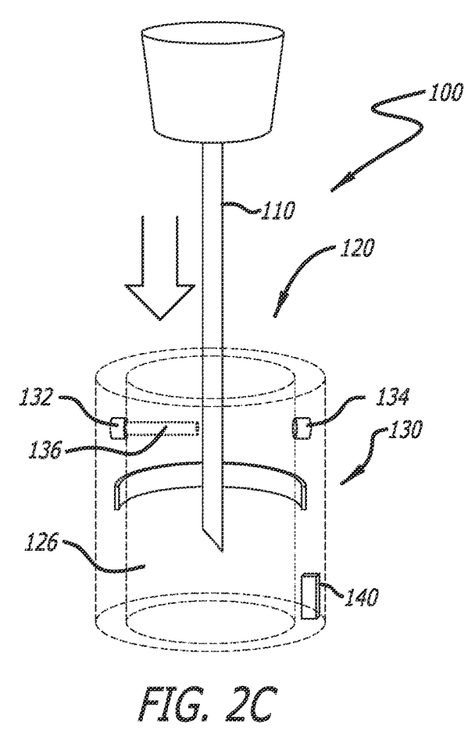

FIGS. 2B-2C illustrates a cross sectional view depicting an exemplary method of the magnetizer 120 detecting the medical device 110 within the cavity 126 using the IR detection system 130, in accordance with some embodiments. As illustrated in FIG. 2B, the medical device 110 may be inserted into the magnetizer 120 to be magnetized. As illustrated in FIG. 2C, as the medical device 110 is inserted into the cavity, the medical device 110 may interrupt the IR beam 136. The IR sensor 134 may be configured to (i) detect the interruption of the IR beam 136 and (ii) transmit the detected interruption to the console 140. The console 140 may generate an alert and wirelessly transmit (e.g., wirelessly transmit) the alert to a computing device or an electronic medical record (EMR) system indicating the medical device 110 has been magnetized. When the medical device 110 is fully removed from the cavity 126, the IR beam 136 will be restored and detected by the IR sensor 134

Figure 3A:
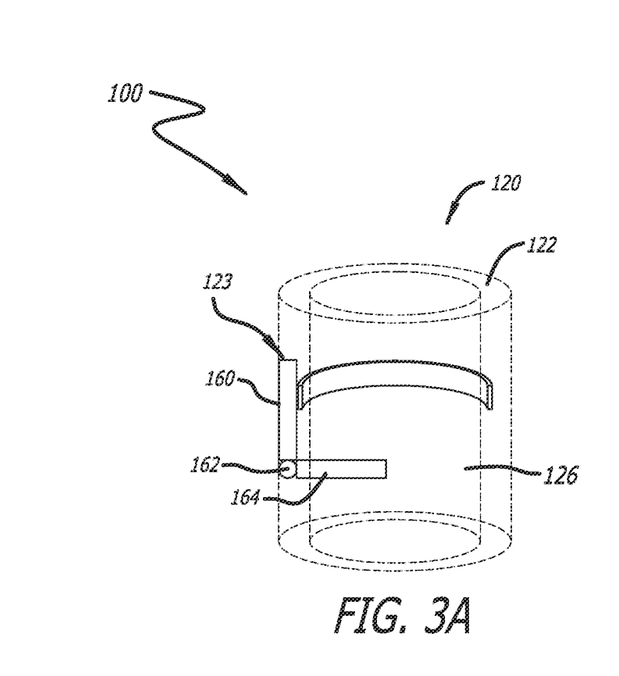
FIGS. 3A-3B illustrates a cross sectional view of a mechanical switch transitioning between a non-magnetized configuration and a magnetized configuration, in accordance with some embodiments.
Figure 3B:
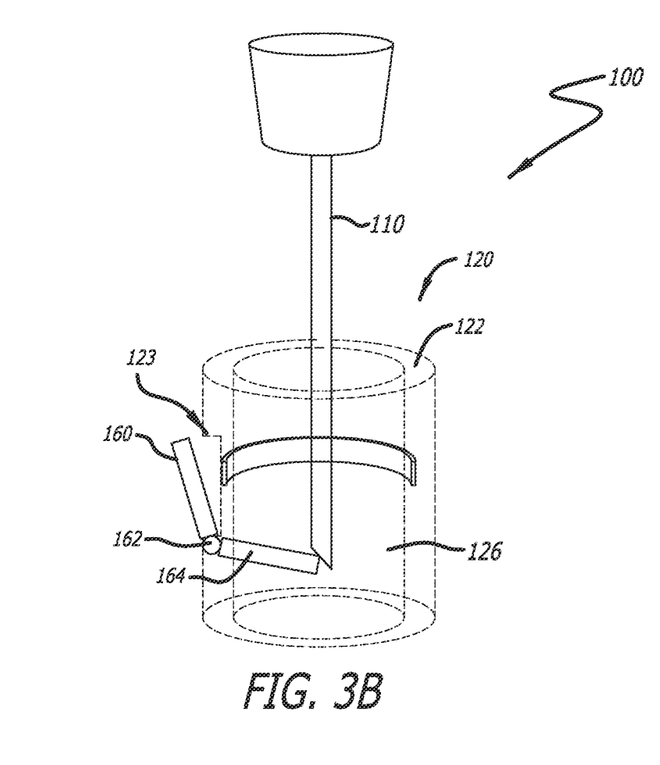

FIGS. 3A-3B illustrates a cross sectional view of the magnetizer 120 including the mechanical switch 160, in accordance with some embodiments. In some embodiments, the magnetizer 120 includes the mechanical switch ("switch") 160 coupled to the magnetizer body 122, the switch 160 configured to indicate to a user when the medical device 110 is within the cavity 126. The switch 160 may reside within a recess 123 in the magnetizer body 122, the switch 160 may be configured to transition from a non-magnetized configuration (i.e., a configuration or position of the switch 160 consistent with the medical device 110 in a non-magnetized state) to a magnetized configuration (i.e., a configuration or position of the switch 160 consistent with the medical device 110 in a magnetized state). The switch 160 may be coupled to a hinge 162, where the hinge 162 may reside at the bottom of the recess 123. The hinge 162 may be configured to allow the switch 160 to transition between the non-magnetized configuration and the magnetized configuration. The hinge 162 may be further coupled to a lever arm 164. The lever arm 164 may be configured to (i) protrude into the cavity 126 and (ii) contact the medical device 110 as the medical device 110 is inserted into the cavity 126. The downward motion of the medical device 110 contacting the lever arm 164 may transition the switch 160 from the non-magnetized configuration to the magnetized configuration. In some embodiments, in the non-magnetized configuration, the switch 160 may reside fully within the recess 123, perpendicular to the lever arm 164 as illustrated in FIG. 3A. In some embodiments, in the magnetized configuration, the switch 160 may extend away from the recess 123 and the magnetizer body 122, as illustrated in FIG. 3B. The lever arm 164 may be configured to deflect or move downward under force. As the medical device 110 is displaced downward within the cavity 126, the medical device 110 contacts the lever arm 164 so that the lever arm 164 deflects downward. As the lever arm 164 deflects downward, the mechanical switch 160 may displace away from the magnetizer 120, signaling that the medical device 110 is (i) within the cavity 126 and (ii) has been magnetized. Once the switch 160 has been transitioned to the magnetized configuration, the switch 160 may be reset to the non-magnetized configuration. Other mechanisms of transitioning the mechanical switch 160 from the non-magnetized configuration to the magnetized configuration are considered.

Figure 4:
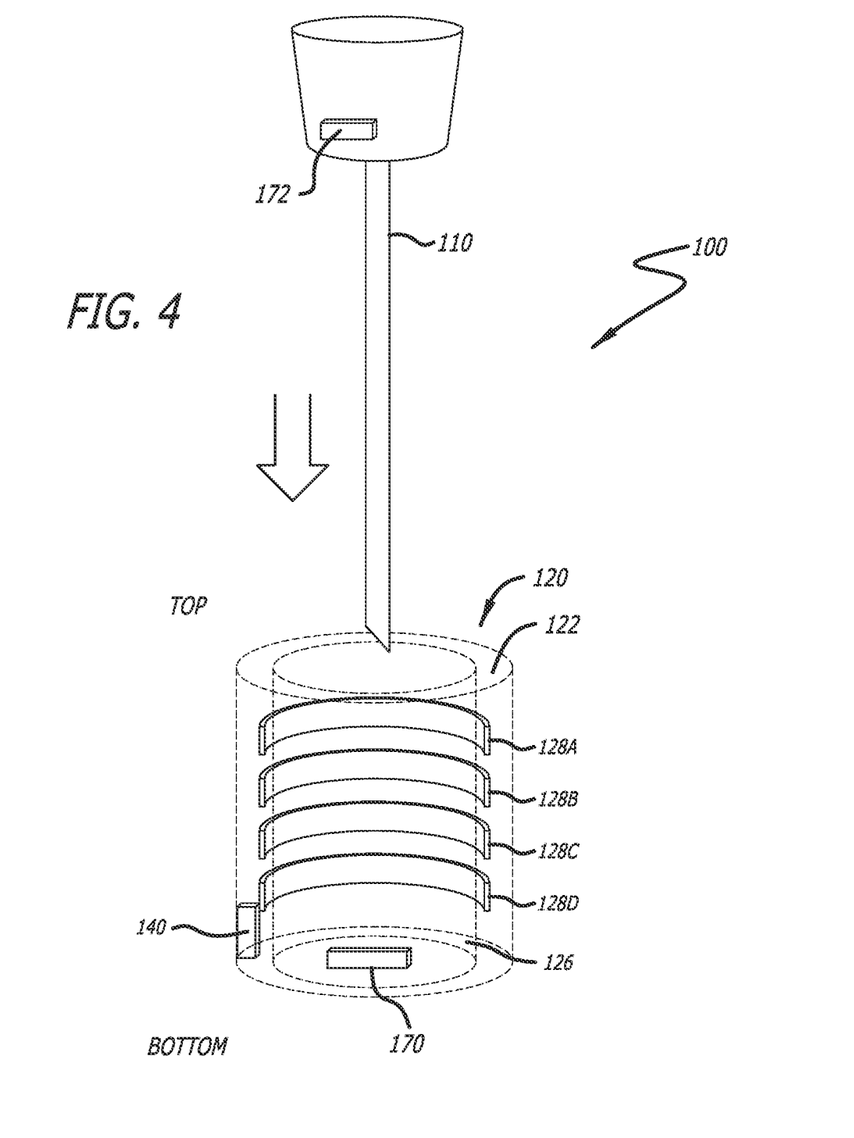
FIG. 4 illustrates a cross sectional view of the magnetizer including a plurality of magnets and a RFID reader, in accordance with some embodiments.

FIG. 4 illustrates a cross sectional view of the magnetizer 120 including the one or more magnets 128A-128D arranged around the cavity 126 and the RFID reader 170, in accordance with some embodiments. In some embodiments, the one or more magnets 128A-128D may be configured to generate the magnetic field within the cavity 126. In some embodiments, the one or more magnets 128A-128D may be configured to generate a monopole magnetic field configured to magnetize ferrous elements disposed within the cavity 126 as the ferrous elements are withdrawn from the magnetic field, thereby imprinting the magnetic signature to the ferrous elements. In some embodiments, the magnetic signature may include a monopole magnetic signature. In some embodiments, the one or more magnets 128A-128D may include one or more electromagnets operatively coupled with an energy source. In some embodiments, the one or more magnets 128A-128D may include one or more magnets that wrap annularly around the cavity 126. In some embodiments, the magnetizer body 122 may include magnetic shielding materials (not shown) configured to contain the magnetic field generated by the one or more magnets 128A-128D within the cavity 126.

In some embodiments, the RFID reader 170 may be in communication with the console 140 or other electronic devices. The RFID reader 170 may be configured to detect one or more RFID tags brought near the magnetizer 120. In some embodiments, the RFID reader 170 may be coupled to the magnetizer 120 and/or may be located within the cavity 126. For example, the RFID reader 170 may be located at a bottom of the cavity 126. In some embodiments, the medical device 110 may include a RFID tag 172 containing information about the medical device 110. Details of an exemplary RFID tag and RFID reader system can be found in US 2018/0310955, published November 1, 2018, which is incorporated by reference in its entirety into this application. The RFID reader 170 may communicate information contained within a detected RFID tag 172 to the console 140, and in some embodiments, the console 140 may communicate the information to additional electronic devices.

Figure 5:
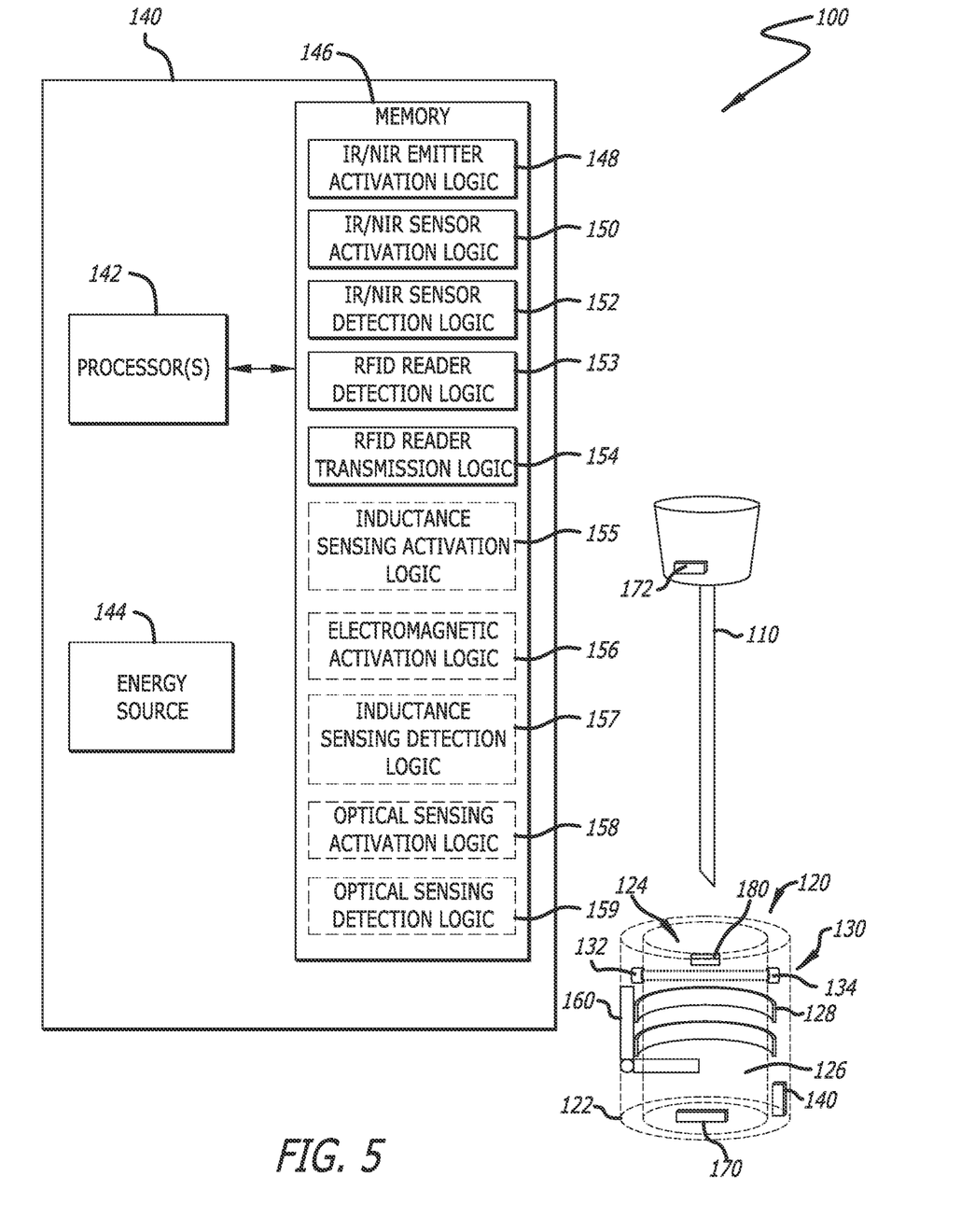
FIG. 5 illustrates a block diagram of some components of the magnetizer including a console, in accordance with some embodiments.

FIG. 5 illustrates a block diagram of some components of the magnetizer 120 including the console 140, in accordance with some embodiments. In some embodiments, the console 140 may include one or more processors 142, an energy source 144, non-transitory computer-readable storage medium ("memory") 146 and a plurality of logic modules. In some embodiments, the energy source 144 may be configured to provide power to the console 140, the IR detection system 130 including the IR/NIR emitters 132, the IR/NIR sensors 134, the one or more sensors 180, and the one or more electromagnets 128. In some embodiments, the energy source 144 may include a rechargeable battery. In some embodiments, the rechargeable battery may be recharged through induction.

In some embodiments, the plurality of logic modules may be configured to include one or more of: an IR/NIR emitter activation logic 148, an IR/NIR sensor activation logic 150, an IR/NIR sensor detection logic 152, an RFID reader detection logic 153, an RFID reader transmission logic 154, and an electromagnet energy source activation logic 156. In some embodiments, the IR/NIR emitter activation logic 148 may be configured to activate the one or more IR/NIR emitters 132 to generate the IR beam 136. In some embodiments, the IR/NIR sensor activation logic 150 may be configured to activate the one or more IR/NIR sensors 134 to detect the IR beam 136. In some embodiments, the IR/NIR sensor detection logic 152 may be configured to detect the IR beam 136 from the one or more emitters 132. In some embodiments, the RFID reader detection logic 153 may be configured to detect the one or more RFID tags brought into communication with the RFID reader 170. In some embodiments, the RFID reader detection logic 153 may be configured to continuously detect the one or more RFID tags, or the RFID reader detection logic 153 may be configured to detect the one or more RFID tags in accordance with a user defined time interval. In some embodiments, the RFID reader detection logic 153 may activate the IR/NIR emitter activation logic 148 and the IR/NIR sensor activation logic 150.

By way of example, a medical device 110 having the RFID tag 172 may be brought into the vicinity of the RFID reader 170. The RFID reader 170 may detect the RFID tag 172 and activate the IR detection system 130. In some embodiments, the RFID reader transmission logic 154 may be configured to wireless transmit the detected RFID tag information to other electronic devices including computing devices, ultrasound probes, the EMR system, or the like. In some embodiments, the RFID reader transmission logic 154 may be configured to transmit an alert, to a computing device, indicating that the medical device 110 has been magnetized. In some embodiments, wherein the one or more magnets 128 are electromagnets, the electromagnetic activation logic 156 may be configured activate the one or more electromagnets 128 to generate the magnetic field within the cavity 126. In some embodiments, where the magnetizer 120 includes the one or more sensors 180 configured to track the medical device 110 using inductive sensing or optical sensing, the plurality of logic modules may include an inductive sensing activation logic 155, an inductive sensing detection logic 157, an optical sensing activation logic 158, and an optical sensing detection logic 159. In some embodiments, the inductive sensing activation logic 155 may be configured to activate the one or more sensors 180 for inductive sensing. In some embodiments, the inductive sensing detection logic 157 may be configured to detect and track the medical device 110 using inductive sensing via the one or more sensors 180. In some embodiments, the optical sensing activation logic 158 may be configured to activate the one or more sensors 180 for optical sensing. In some embodiments, the optical sensing detection logic 159 may be configured to detect and track the medical device 110 using optical sensing via the one or more sensors 180.

Figure 6A:
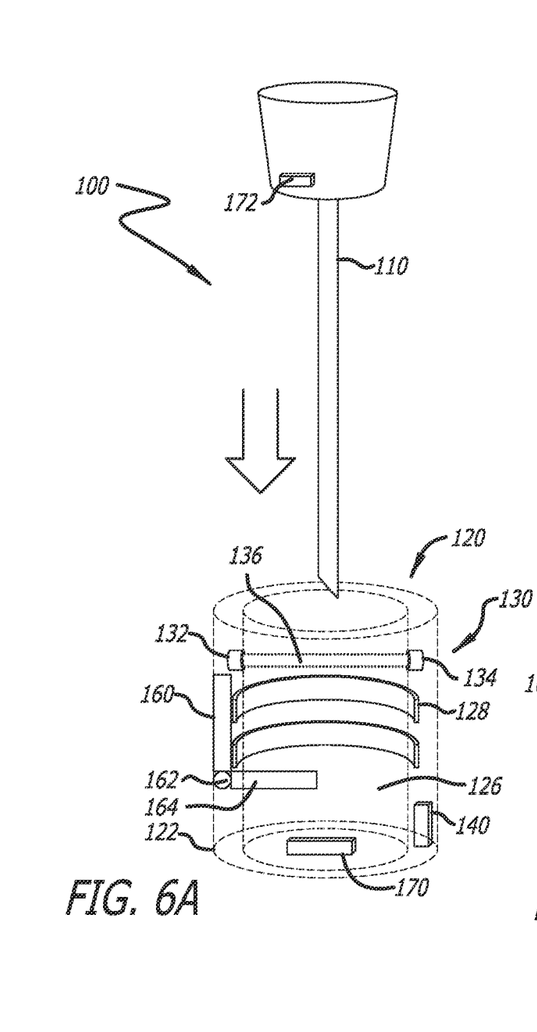
FIGS. 6A-6C illustrates a cross sectional view of an exemplary method of providing a magnetic signature to the medical device using the magnetizer, in accordance with some embodiments.
Figure 6B:
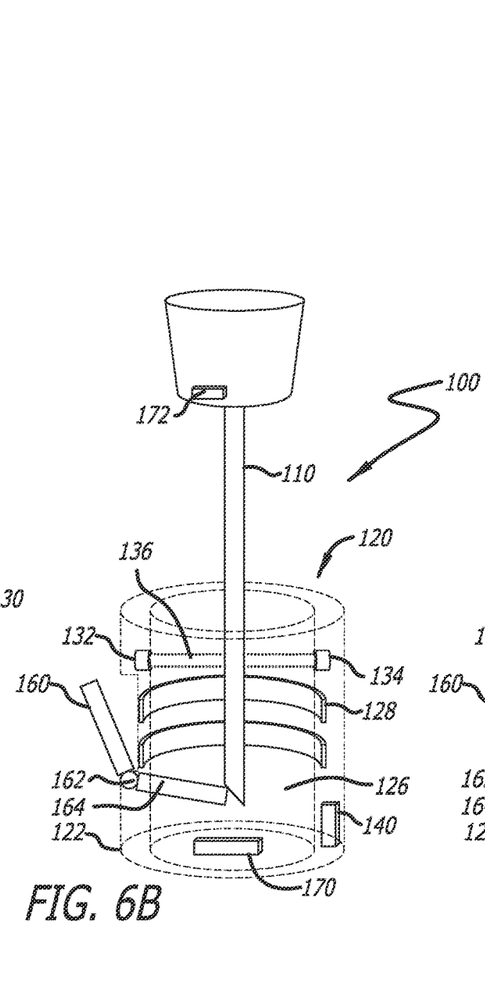
Figure 6C:
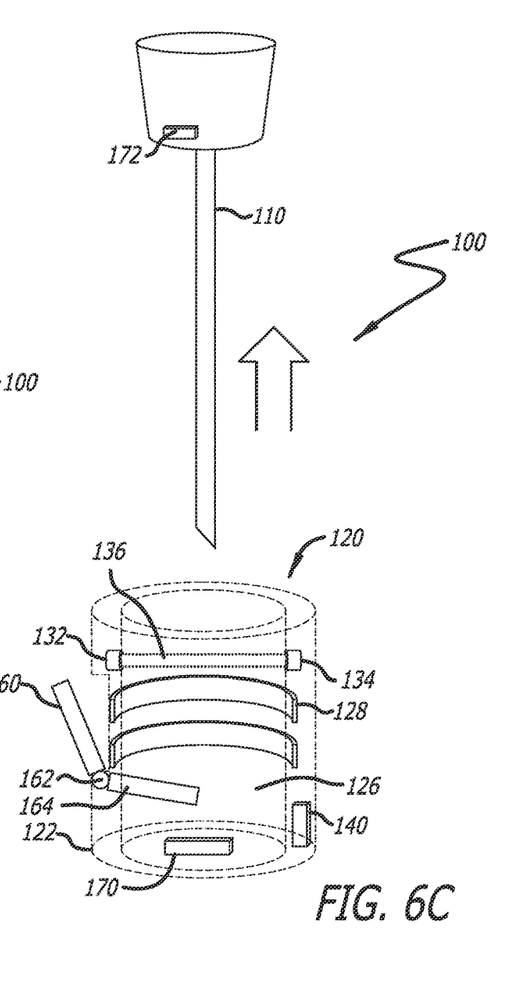

FIGS. 6A-6C illustrate a cross sectional views depicting an exemplary method of providing a magnetic signature to the medical device 110 using the magnetizer 120, in accordance with some embodiments. In some embodiments, the magnetizer 120 includes the one or more magnets 128, the mechanical switch 160, the IR detection system 130, and the RFID reader 170, as described above. The mechanical switch 160 may be in the non-magnetized configuration and the IR/NIR sensors 134 may detect an unbroken IR beam 136 from the IR/NIR emitters 132, as illustrated in FIG. 6A. The medical device 110 having the RFID tag 172 may be inserted into the cavity 126 of the magnetizer 120, breaking the IR beam 136. As illustrated in FIG. 6B, the medical device 110 may be inserted into the cavity 126 wherein the IR/NIR sensors 134 may detect the broken IR beam from the IR/NIR emitters 132, and the medical device may contact the lever arm 164. The RFID reader 170 may detect the RFID tag 172 of the medical device 110 and communicate the information contained in the RFID tag 172 to the console 140. The mechanical switch 160 may transition from the non-magnetized configuration to the magnetized configuration. During removal of the medical device 110 from the cavity 126, the one or more magnets 128 may magnetize the medical device 110 with the magnetic signature. When the medical device 110 is fully removed from the cavity 126, the IR/NIR sensors 134 may detect the restored IR beam 136 from the IR/NIR emitters 132. The mechanical switch 160 may indicate the medical device 110 has been magnetized via the mechanical switch 160 having transitioned to the magnetized configuration. Once the medical device 110 has been fully removed from the cavity 126, the mechanical switch 160 may be reset to the non-magnetized configuration, and the IR beam 136 may be restored so as to be detected by the IR/NIR sensors 134.

Figure 7:
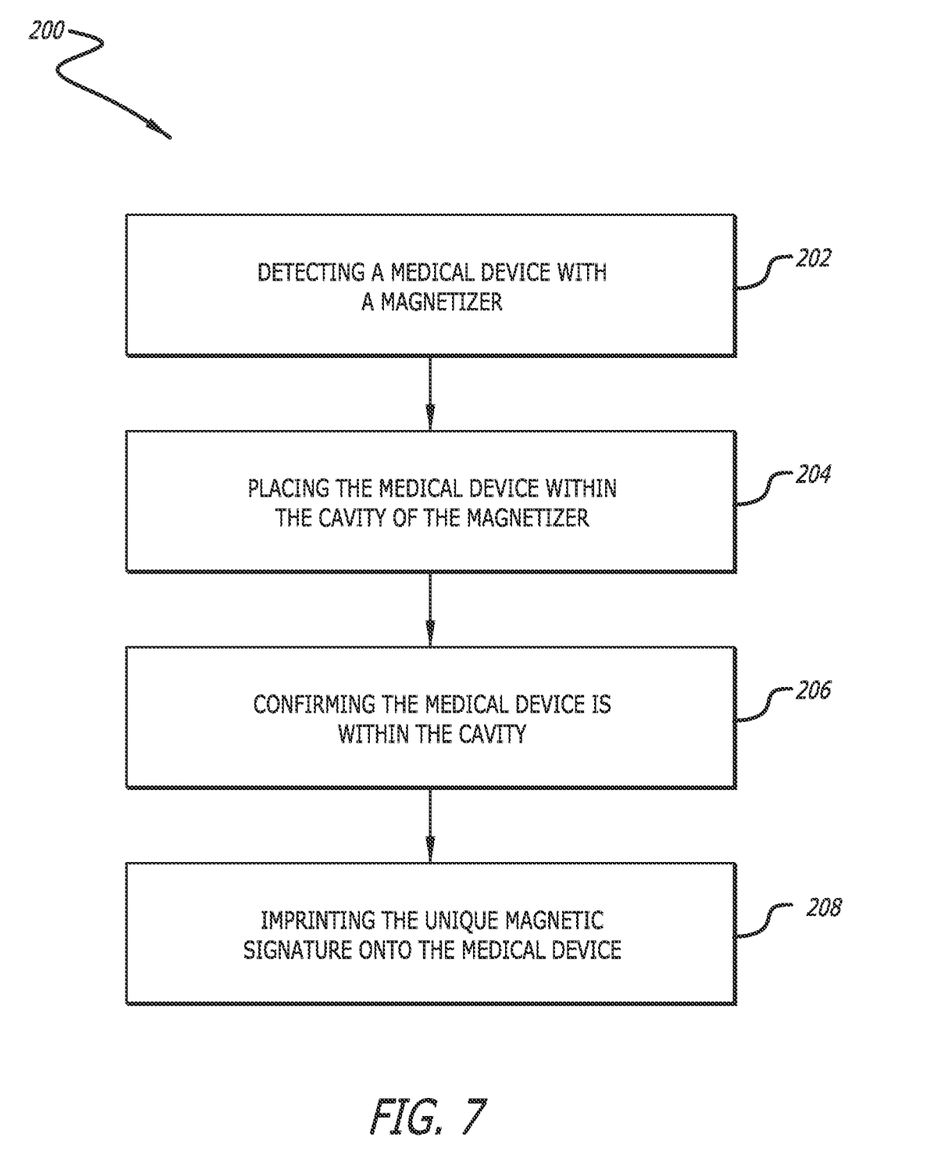
FIG. 7 illustrates a flow chart of the exemplary method of providing a magnetic signature to a medical device using the magnetizer, in accordance with some embodiments.

FIG. 7 illustrates a flow chart of an exemplary method 200 of providing a magnetic signature to the medical device 110 using the magnetizer 120, in accordance with some embodiments. In some embodiments, the method 200 includes detecting the medical device 110 with the magnetizer 120 (block 202). In some embodiments, detecting the medical device 110 includes detecting the medical device 110 with the RFID reader 170 coupled to the magnetizer 120. In some embodiments, detecting the medical device 110 with the RFID reader 170 includes detecting the RFID tag 172 coupled to the medical device 110. In some embodiments, detecting the medical device 110 includes using the one or more sensors 180 to detect the medical device 110 via inductive sensing or optical sensing.

The method 200 further includes placing the medical device 110 within the cavity 126 of the magnetizer 120 (block 204). In some embodiments, placing the medical device 110 within the cavity 126 includes slidably inserting, dipping or otherwise displacing the medical device 110 into the cavity 126. The method 200 includes confirming the medical device 110 is within the cavity 126 (block 206). In some embodiments, confirming the medical device 110 is within the cavity 126 includes confirming the medical device 110 is within the cavity via the IR detection system 130. In some embodiments, confirming with the IR detection system 130 includes confirming via the medical device 110 interrupting the IR beam 136. In some embodiments, confirming the medical device 110 is within the cavity 126 includes confirming via the mechanical switch 160 transitioning from the non-magnetized configuration to the magnetized configuration. In some embodiments, the medical device 110 contacting the lever arm 164 transitions the mechanical switch 160 from the non-magnetized configuration to the magnetized configuration.

The method 200 further includes imprinting the magnetic signature onto medical device 110 (block 208). In some embodiments, imprinting the magnetic signature onto the medical device 110 includes the one or more magnets 128 imprinting the magnetic signature onto the medical device 110. In some embodiments, the process of withdrawing the medical device 110 from the cavity 126 imprints the magnetic signature onto the medical device 110.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A magnetizer system for use with a medical device including ferrous elements, the magnetizer system comprising:
   a magnetizer having a magnetizer body defining a cavity, the magnetizer body having a body opening in communication with the cavity, the magnetizer body including one or more magnets configured to generate a magnetic field configured to imprint a magnetic signature on the ferrous elements within the cavity, the magnetic signature configured to differentiate the medical device from other medical devices, wherein the magnetic signature includes a monopole magnetic signature; and
   one or more mechanisms configured to detect a presence of the medical device.

2. The magnetizer system according to claim 1, wherein the one or more mechanisms include an infrared detection system having one or more infrared emitters configured to generate an infrared beam across the cavity and one or more infrared sensors configured to detect the infrared beam, the one or more infrared emitters, and the one or more infrared sensors in communication with a console.

3. The magnetizer system according to claim 2, wherein the magnetizer includes one or more sensors in communication with the console, the one or more sensors configured to detect and track the medical device using inductive sensing or optical sensing.

4. The magnetizer system according to claim 2, wherein the console includes one or more processors, an energy source, a non-transitory computer-readable medium, and a plurality of logic modules.

5. The magnetizer system according to claim 4, wherein the one or more magnets include one or more electromagnets in communication with the energy source.

6. The magnetizer system according to claim 4, wherein the console is in wireless communication with one or more computing devices or an electronic medical record system.

7. The magnetizer system according to claim 4, wherein the plurality of logic modules, when executed by the one or more processors, are configured to perform operations including:
   activating the one or more infrared sensors and the one or more infrared emitters;
   detecting an RFID tag of the medical device;
   detecting the infrared beam from the one or more infrared emitters;
   activating the one or more infrared sensors; and
   detecting the medical device using the one or more infrared sensors by inductive sensing or optical sensing.

8. The magnetizer system according to claim 1, wherein the one or more mechanisms include a mechanical switch configured to transition between a non-magnetized configuration and a magnetized configuration.

9. The magnetizer system according to claim 8, wherein the mechanical switch includes a hinge coupled to each of the mechanical switch and a lever arm, the lever arm protruding into the cavity and configured to be contacted by the medical device to transition the mechanical switch from the non-magnetized configuration to the magnetized configuration.

10. The magnetizer system according to claim 9, wherein the mechanical switch resides within a recess within the magnetizer body.

11. The magnetizer system according to claim 10, wherein the non-magnetized configuration includes the mechanical switch perpendicular to the lever arm and residing fully within the recess.

12. The magnetizer system according to claim 10, wherein the magnetized configuration includes the mechanical switch moved away from the recess and the magnetizer body.

13. The magnetizer system according to claim 1, wherein the magnetizer includes a RFID reader coupled to the magnetizer body or contained within the cavity, the RFID reader in communication with a console.

14. The magnetizer system according to claim 13, wherein the medical device includes a RFID tag configured to be detected by the RFID reader.

15. The magnetizer system according to claim 1, wherein the medical device including the ferrous elements is selected from the group consisting of a needle, a catheter, and combinations thereof.

16. The magnetizer system according to claim 1, wherein the magnetic signature includes one or more of model name, model number, dimensional information, manufacturing information, and serial number.

17. A magnetizer system for use with a medical device including ferrous elements, the magnetizer system comprising:
a magnetizer having a magnetizer body defining a cavity, the magnetizer body having a body opening in communication with the cavity, the magnetizer body including one or more magnets configured to generate a magnetic field configured to imprint a magnetic signature on the ferrous elements within the cavity, the magnetic signature configured to differentiate the medical device from other medical devices; and
one or more mechanisms configured to detect a presence of the medical device, wherein the one or more mechanisms include an infrared detection system having one or more infrared emitters configured to generate an infrared beam across the cavity and one or more infrared sensors configured to detect the infrared beam, the one or more infrared emitters, and the one or more infrared sensors in communication with a console.

18. The magnetizer system according to claim 17, wherein the magnetizer includes one or more sensors in communication with the console, the one or more sensors configured to detect and track the medical device using inductive sensing or optical sensing.

19. The magnetizer system according to claim 17, wherein the console includes one or more processors, an energy source, a non-transitory computer-readable medium, and a plurality of logic modules.

20. The magnetizer system according to claim 19, wherein the one or more magnets include one or more electromagnets in communication with the energy source.

21. The magnetizer system according to claim 19, wherein the console is in wireless communication with one or more computing devices or an electronic medical record system.

22. The magnetizer system according to claim 19, wherein the plurality of logic modules, when executed by the one or more processors, are configured to perform operations including:

activating the one or more infrared sensors and the one or more infrared emitters;
detecting an RFID tag of the medical device;
detecting the infrared beam from the one or more infrared emitters;
activating the one or more infrared sensors; and
detecting the medical device using the one or more infrared sensors by inductive sensing or optical sensing.

23. A magnetizer system for use with a medical device including ferrous elements, the magnetizer system comprising:
a magnetizer having a magnetizer body defining a cavity, the magnetizer body having a body opening in communication with the cavity, the magnetizer body including one or more magnets configured to generate a magnetic field configured to imprint a magnetic signature on the ferrous elements within the cavity, the magnetic signature configured to differentiate the medical device from other medical devices; and
one or more mechanisms configured to detect a presence of the medical device, wherein the one or more mechanisms include a mechanical switch configured to transition between a non-magnetized configuration and a magnetized configuration.

24. The magnetizer system according to claim 23, wherein the mechanical switch includes a hinge coupled to each of the mechanical switch and a lever arm, the lever arm protruding into the cavity and configured to be contacted by the medical device to transition the mechanical switch from the non-magnetized configuration to the magnetized configuration.

25. The magnetizer system according to claim 24, wherein the mechanical switch resides within a recess within the magnetizer body.

26. A magnetizer system for use with a medical device including ferrous elements, the magnetizer system comprising:
a magnetizer having a magnetizer body defining a cavity, the magnetizer body having a body opening in communication with the cavity, the magnetizer body including one or more magnets configured to generate a magnetic field configured to imprint a magnetic signature on the ferrous elements within the cavity, the magnetic signature configured to differentiate the medical device from other medical devices, wherein the magnetic signature includes one or more of model name, model number, dimensional information, manufacturing information, and serial number; and
one or more mechanisms configured to detect a presence of the medical device.

* * * * *